(12) United States Patent
Ochs et al.

(10) Patent No.: US 9,107,635 B2
(45) Date of Patent: *Aug. 18, 2015

(54) METHODS AND SYSTEMS FOR ALERTING PRACTITIONERS TO PHYSIOLOGICAL CONDITIONS

(71) Applicant: COVIDIEN LP, Mansfield, MA (US)

(72) Inventors: James Ochs, Seattle, WA (US); Scott Amundson, Oakland, CA (US); Keith Batchelder, New York, NY (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/286,269

(22) Filed: May 23, 2014

(65) Prior Publication Data

US 2015/0018653 A1    Jan. 15, 2015

Related U.S. Application Data

(62) Division of application No. 12/388,123, filed on Feb. 18, 2009, now Pat. No. 8,750,953.

(60) Provisional application No. 61/066,182, filed on Feb. 19, 2008.

(51) Int. Cl.
| | |
|---|---|
| *A61B 5/00* | (2006.01) |
| *G08B 29/00* | (2006.01) |
| *G08B 21/00* | (2006.01) |
| *G08B 23/00* | (2006.01) |
| *G08B 21/04* | (2006.01) |
| *A61B 5/0205* | (2006.01) |
| *A61B 5/1455* | (2006.01) |
| *A61B 5/145* | (2006.01) |
| *A61B 5/024* | (2006.01) |

(52) U.S. Cl.
CPC ............ *A61B 5/4818* (2013.01); *A61B 5/0205* (2013.01); *A61B 5/14551* (2013.01); *A61B 5/7278* (2013.01); *A61B 5/7282* (2013.01); *A61B 5/742* (2013.01); *A61B 5/7405* (2013.01); *A61B 5/746* (2013.01); *G08B 21/0453* (2013.01); *A61B 5/02416* (2013.01); *A61B 5/1455* (2013.01); *A61B 5/14542* (2013.01)

(58) Field of Classification Search
CPC ............ A61B 5/1455; A61B 5/14551; A61B 5/14542; A61B 5/4818
USPC ............... 600/323–341; 340/511, 540, 573.1; 128/204.23
See application file for complete search history.

(56) References Cited

U.S. PATENT DOCUMENTS

| | | | | |
|---|---|---|---|---|
| 5,632,272 | A * | 5/1997 | Diab et al. ................... | 600/323 |
| 5,865,736 | A * | 2/1999 | Baker et al. .................. | 600/323 |
| 6,584,336 | B1 * | 6/2003 | Ali et al. ...................... | 600/323 |
| 6,754,516 | B2 * | 6/2004 | Mannheimer ................ | 600/323 |

(Continued)

*Primary Examiner* — Devin Henson
(74) *Attorney, Agent, or Firm* — Fletcher Yoder PC

(57) ABSTRACT

Embodiments of the present disclosure provide systems and methods for monitoring a patient to produce a signal representing a blood oxygen concentration. The signal may be analyzed to determine the presence of one or more sleep apnea events, and an integral of the signal may be calculated if the signal is outside of a set range or threshold. A practitioner may choose to be informed of the presence of sleep apnea events if the blood oxygen concentration is less then a preset limit, if an upper limit has been reached for an integral representing the severity of the oxygen deprivation over time, or anytime sleep apnea events may be present in the signal.

20 Claims, 9 Drawing Sheets

(56) References Cited

U.S. PATENT DOCUMENTS

| | | | |
|---|---|---|---|
| 6,760,608 B2 * | 7/2004 | Lynn | 600/324 |
| 7,030,749 B2 * | 4/2006 | Al-Ali | 340/511 |
| 8,750,953 B2 * | 6/2014 | Ochs et al. | 600/323 |

* cited by examiner

METHODS AND SYSTEMS FOR ALERTING PRACTITIONERS TO PHYSIOLOGICAL CONDITIONS

CROSS-REFERENCE TO RELATED APPLICATIONS

This application is a divisional of U.S. application Ser. No. 12/388,123, filed Feb. 18, 2009, which claims priority to U.S. Provisional Application No. 61/066,182, filed Feb. 19, 2008, the disclosures of which are hereby incorporated in their entirety for all purposes.

BACKGROUND

The present disclosure relates to a system and method for alerting users to physiological conditions, more particularly, to a medical device configured to inform a user of the presence of patterns that may indicate the presence of sleep apnea.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Obstructive sleep apnea is a condition in which a patient's breathing is temporarily interrupted when sleeping. The condition is believed to be associated with increased fat deposits in the neck, which commonly occur as a patient ages. These increased fat deposits may lead to a narrowing of the airway. When muscle tone diminishes during sleep, the narrowed airway can collapse during inhalation, effectively blocking air movement. The patient attempts to inhale more deeply, further collapsing the airway. With no air movement, the oxygen level in the patient's bloodstream falls, finally reaching a point where the patient is aroused out of sleep. Upon arousal, the muscle tone increases, the airway opens, and air flow to the lungs is precipitously restored. The patient hyperventilates, which quickly restores the blood oxygen levels to normal levels. The period of arousal may be brief, so the patient is often unaware that the event took place. The patient returns to sleeping, and the cycle often repeats.

Over the years, this repeating cycle of low oxygen levels in the bloodstream can damage the heart and lead to other medical complications. Obstructive sleep apnea is believed to be one of the most common disorders in the United States. However, unlike other common medical disorders, such as diabetes, no simple diagnostic test has been developed to determine if a patient has sleep apnea. Tests do exist that can be used to diagnose sleep apnea, but the tests typically involve an overnight sleep study, which can be costly and inconvenient. The need for a simple, low-cost diagnostic test has led medical personnel to try less expensive techniques, such as pulse oximetry, to diagnose the presence of obstructive sleep apnea.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Medical devices may be used to obtain or calculate signals representing physiological parameters from patients, such as $SpO_2$ signals related to a patient's level of blood oxygenation. However, these signals, which are sequences of numerical values of a physiological parameter over time, may have too much information or noise to be effectively used in the diagnosis or treatment of certain medical conditions. Accordingly, the signals may be processed to generate alerts, which may provide a more useful representation of the status of the medical condition. Embodiments of the present techniques provide methods that may be useful for generating indicators of a physiological status, based on a signal representing the blood oxygen saturation (SpO2) level in a patient and, thus, alerting a practitioner to physiologically important conditions.

The indicators may be directly related to the presence of obstructive sleep apnea and may assist practitioners in the diagnosis and treatment of this condition. In embodiments, $SpO_2$ data collected on a pulse oximeter may be used to calculate or determine the alerts. The relative simplicity of this device could enhance the diagnosis of obstructive sleep apnea by allowing patients to take diagnostic equipment home for use overnight and return the equipment to a practitioner for analysis and diagnosis.

Previous studies have examined the possibility of generating a single index reflective of sleep apnea from pulse oximetry data, such as an airway instability index, but many have used schemes that may either be challenging for a practitioner to implement in a treatment setting or overly sensitive to changes. As embodiments may be implemented using current medical devices, their implementation may be easier to explain and use than a more complex calculation for an airway instability index.

Figure 1:
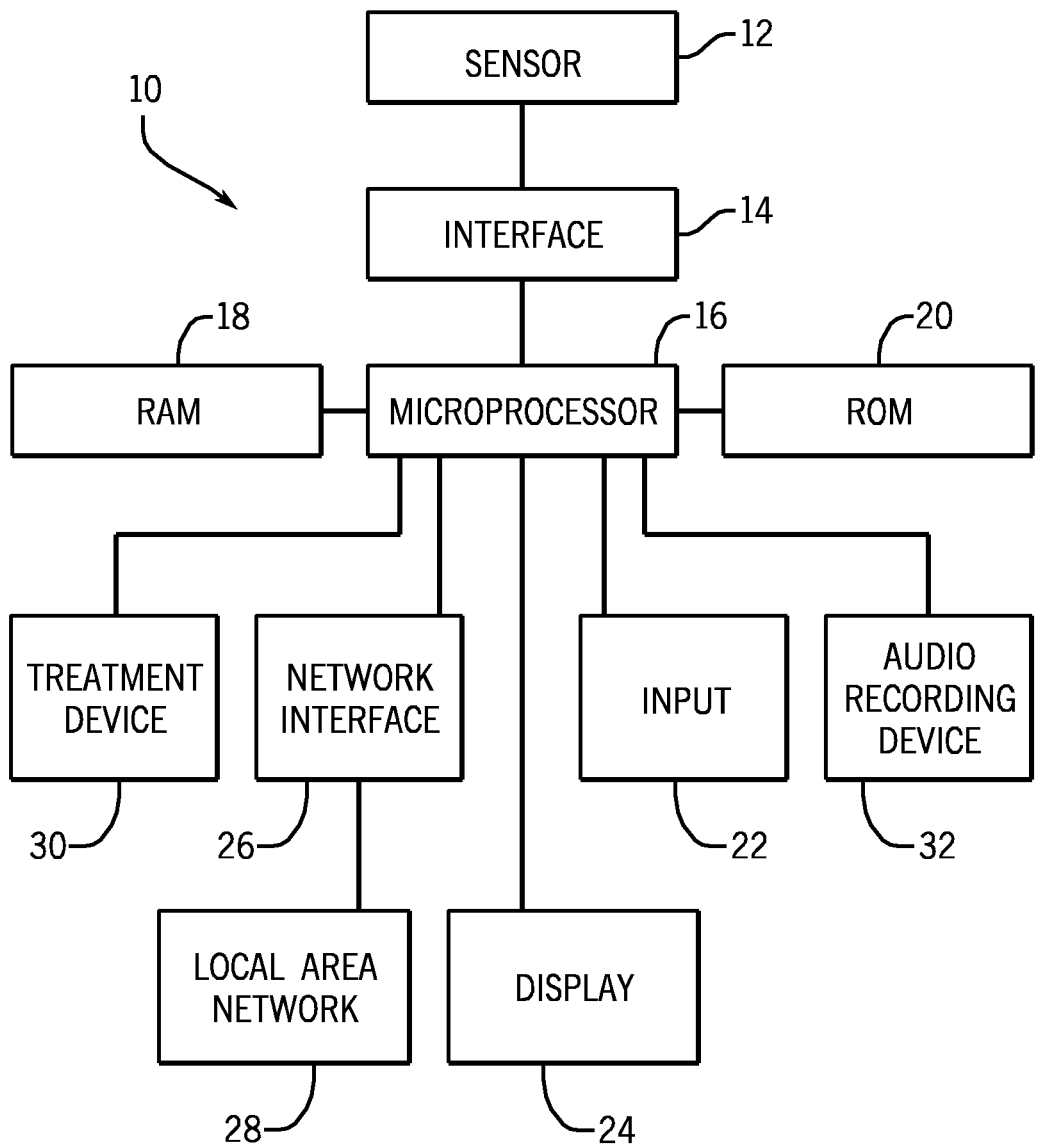
FIG. 1 is a block diagram of a system that may be used for the diagnosis and treatment of sleep apnea, in accordance with an embodiment.

FIG. 1 is a block diagram of a medical device 10, which may be used in embodiments of the present disclosure. The medical device 10 may have a sensor 12 for the collection of a signal representing a physiological parameter. In embodiments, the sensor 12 may be an optical sensor used with a pulse oximeter for the measurement of oxygen saturation in the bloodstream. The signal from the sensor 12 may be conditioned by an interface 14 prior to being utilized by a microprocessor 16. The microprocessor 16 may be coupled to random access memory (RAM) 18 and/or read-only memory (ROM) 20. The RAM 18 may be used to store the signals from the sensor 12 and the results of calculations that the microprocessor 16 performs. The ROM 20 may contain code to direct the microprocessor 16 in collecting and processing the signal. The microprocessor 16 may be coupled to an input device 22 which may be used for local entry of control and calculation parameters for the medical device 10. A display unit 24 may be coupled to the microprocessor 16 to display the results the microprocessor 16 has generated from the signal.

The microprocessor 16 may also be coupled to a network interface 26 for the transfer of data from the microprocessor 16 to devices coupled to a local area network 28. The transferred data may, for example, include signal data, indices including an airway instability index, alert signals, alarm signals, or any combination thereof. The transferred data may also consist of control signals from the devices on the local area network 28, for example, to instruct the medical device 10 to send signal data, or other information, to a device on the local area network 28.

In an embodiment, the medical device 10 may be used to alert a practitioner to a physiological condition using data collected from the sensor 12. The alert may be output to the display unit 24 or sent to a network device on the local area network 28. The processing may take place in real time, or may be run after the data collection may be completed for later identification of the physiological condition.

In another embodiment, a network device located on the local area network 28 may be configured to alert a practitioner to the presence of a physiological condition using the data collected from the sensor 12. In this embodiment, the network device may request that the signal be sent from the medical device 10 through the network interface 26. As for the embodiment discussed above, the network device may be used to either determine the alert signal in real time or to process a previously collected signal for later identification of the physiological condition.

In either of the embodiments above, the alert signals may appear on devices on the local area network 28, for example, a patient monitoring screen in an ICU. Alternatively, the alert signals may appear on the display unit 24 of the medical device 10. In embodiments, an alert signal may be activated in both locations using the results from either a local calculation on the medical device 10 or from a remote calculation on a network device coupled to the local area network 28.

The microprocessor 16 may also be coupled to a treatment device 30. For example, the treatment device 30 may be a positive pressure mask used to supply air at an increased pressure to maintain an open airway. In an embodiment, the treatment device 30 may be controlled by the microprocessor 16, for example, activating the treatment device 30 to open an airway based on the alert signals. This control may be useful in helping to confirm a diagnosis of obstructive sleep apnea, as restoration of the airway may restore blood oxygen levels to more normal levels.

A diagnosis of sleep apnea may also be aided by the sound the patient may be making during the sleep apnea events. For example, cessation of breathing following by a sudden gasping intake of breath may provide or confirm the diagnosis. However, such events may be irregularly spaced or may be separated by large time intervals, making any continuous audio recording of the patient tedious and/or expensive to analyze. An audio recording device 32 may be coupled to the microprocessor 16 for recording sounds made by the patient. In an embodiment, the microprocessor 16 may activate the audio recording device 32 based on the alert signals and record patient sounds when a sleep apnea event may be likely to be occurring. When combined with the alert signals, the sound recordings are likely to provide a positive diagnosis of obstructive sleep apnea.

Exemplary embodiments activate alert signals on the value of two general conditions. The first condition may be the presence or absence of clusters in the $SpO_2$ signal, as discussed below. The second condition may be the value of an integral calculated from the absolute level of the $SpO_2$ signal in comparison to previous set limits. The determination of these conditions is discussed in detail with respect to FIG. 2.

Figure 2:
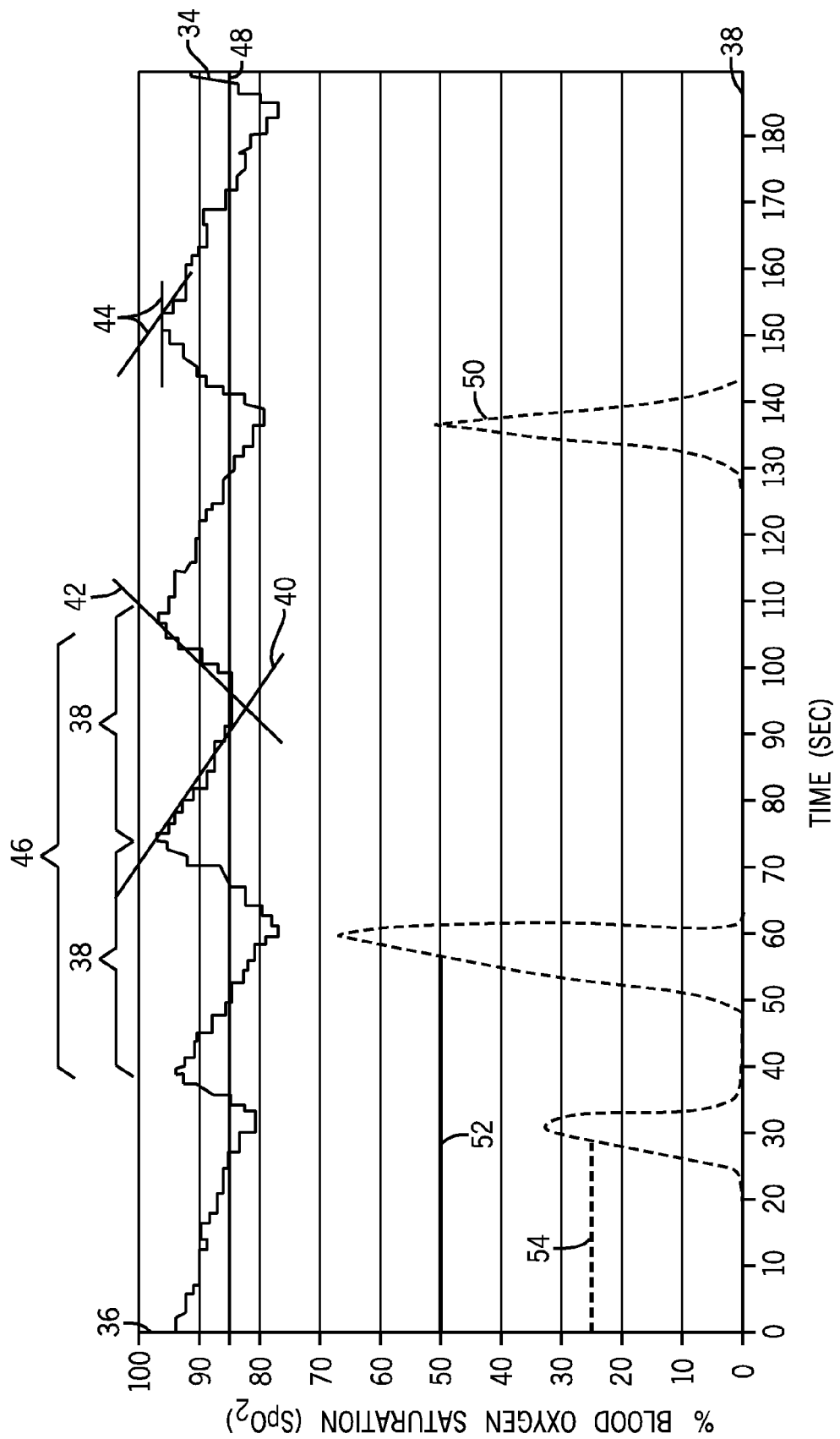
FIG. 2 is a chart of an $SpO_2$ signal over time, illustrating techniques for identifying desaturation patterns, clusters, and low oxygen levels in a patient, in accordance with an embodiment.

FIG. 2 is a chart of a sequence of values representing the blood oxygen saturation ($SpO_2$) of a patient over time, i.e., an SpO2 signal 34. In this chart, a left vertical axis 36 represents the $SpO_2$ level. A horizontal axis 38 represents the time in seconds. In an embodiment, a pattern analysis method may be used to identify obstructive sleep apnea and calculate an airway instability index from the $SpO_2$ signal 34. The method takes advantage of the fact that during each sleep apnea event, e.g., during a single one of the desaturation patterns 38, the blood oxygen level falls slowly, as indicated by reference numeral 40, as oxygen stores in the body are used up and then sharply recovers, as indicated by reference numeral 42, as the patient is aroused and hyperventilates.

The determination of the presence of one or more desaturation patterns 38 may be performed by any number of different techniques. For example, in an embodiment, a single one of the desaturation patterns 38 may be identified by a combination of events, such as when a continuously calculated slope 44 of the $SpO_2$ signal 34 drops to a previously selected value, e.g. −1.5 and the $SpO_2$ signal crosses a predetermined $SpO_2$ level, e.g., 85%. In another embodiment, desaturation patterns 38 may be identified using the methods discussed in U.S. Pat. No. 6,760,608 (hereinafter the '608 patent), incorporated by reference for all purposes as if fully set forth herein. Any number of different numerical values may be used in the determination of the presence of desaturation patterns 38, for example, in embodiments, the value of the slope 44, selected to indicate the start of one of the desaturation patterns 38, may be −0.5, −1.0, −1.5, −2, or any value in between. Further, in embodiments, the predetermined $SpO_2$ level used to indicate the start of one of the desaturation patterns 38 may be 95%, 90%, 85%, 80%, 75%, or any appropriate value in between.

Recurring sleep apnea events may often occur in groups of at least two successive desaturation patterns 38, called a cluster 46. The severity of the apnea may be determined from, for example, the number of desaturation patterns 38 in each cluster 46, the time between each one of the desaturation patterns 38, the slope of the drop 40 in the blood oxygen level during each one of the desaturation patterns 38 or the slope of the recovery 42 of the blood oxygen level as each one of the desaturation patterns 38 ends, among others.

Figure 3:
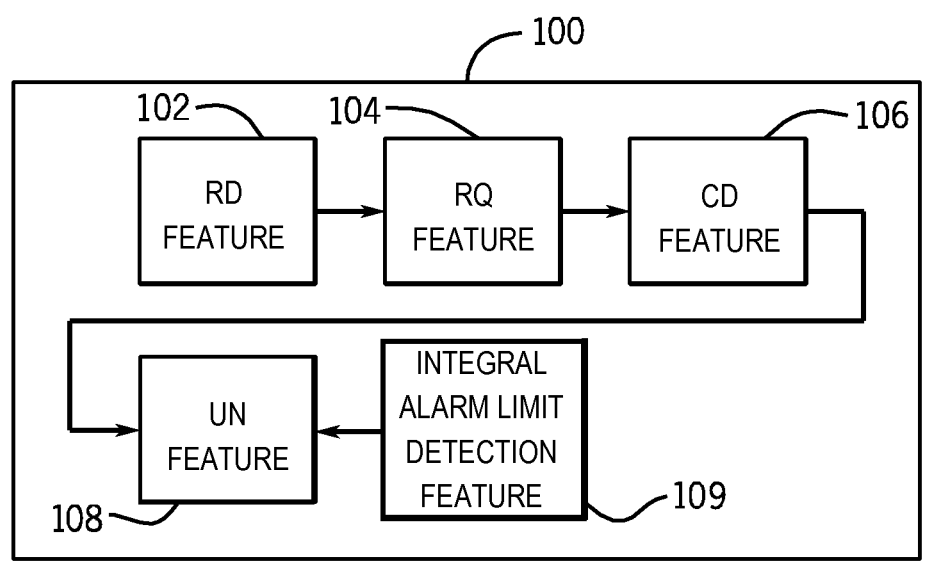
FIG. 3 is a block diagram of an exemplary cluster detection portion of a system.

In an embodiment, a medical monitor or electronic device may include a module or a set of programming instructions for detecting desaturation patterns or clusters and for detecting desturation below certain limits. FIG. 3 is a block diagram of an exemplary cluster detection unit 100 that includes a reciprocation detection (RD) feature 102, a reciprocation qualification (RQ) feature 104, a cluster determination (CD) feature 106, an integral alarm limit detection feature 109, and a user notification (UN) feature 108. Each of these components and the coordination of their functions will be discussed in further detail below.

It should be noted that, in order to detect certain data patterns, embodiments of the present disclosure may utilize systems and methods such as those disclosed in U.S. Pat. Nos. 6,760,608, 6,223,064, 5,398,682, 5,605,151, 6,748,252, U.S. application Ser. No. 11/455,408 filed Jun. 19, 2006, U.S. application Ser. No. 11/369,379 filed Mar. 7, 2006, and U.S. application Ser. No. 11/351,787 filed Feb. 10, 2006. Accordingly, U.S. Pat. Nos. 6,760,608, 6,223,064, 5,398,682, 5,605,151, 6,748,252, U.S. application Ser. No. 11/455,408 filed Jun. 19, 2006, U.S. application Ser. No. 11/369,379 filed Mar. 7, 2006, and U.S. application Ser. No. 11/351,787 filed Feb. 10, 2006 are each incorporated herein by reference in their entirety for all purposes.

Figure 4:
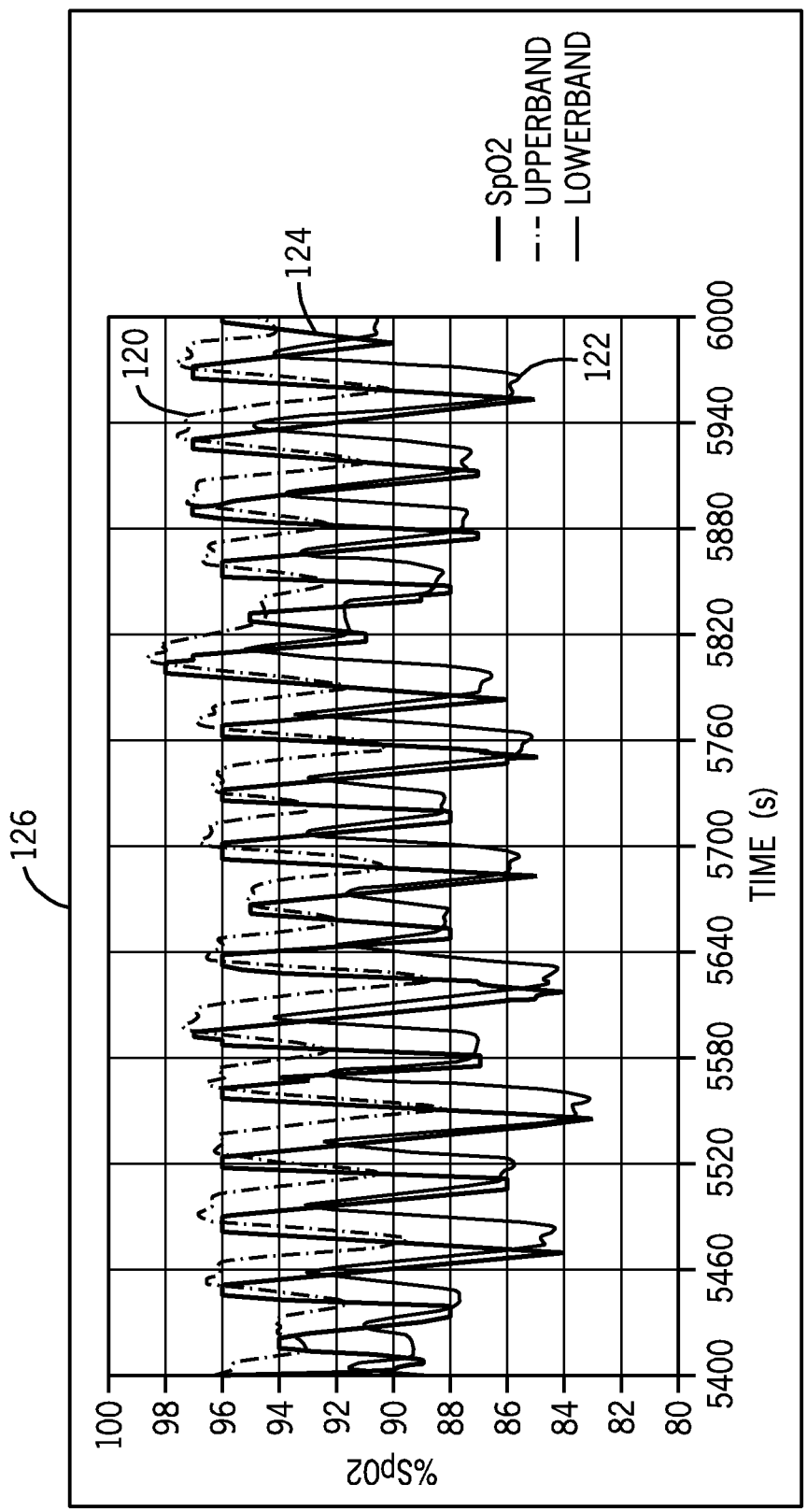
FIG. 4 is an exemplary graph of $SpO_2$ trend data with an upper band and lower band based on mean and standard deviation values.

The RD feature 102 may be capable of performing an algorithm for detecting reciprocations in a data trend. Specifically, the algorithm of the RD feature 102 may perform a statistical method to find potential reciprocation peaks and nadirs in a trend of $SpO_2$ data. A nadir may be defined as a minimum $SpO_2$ value in a reciprocation. The peaks may include a rise peak (e.g., a maximum $SpO_2$ value in a reciprocation that occurs after the nadir) and/or a fall peak (e.g., a maximum $SpO_2$ value in a reciprocation that occurs before the nadir). Once per second, the RD feature 102 may calculate a 12 second rolling mean and standard deviation of the $SpO_2$ trend. Further, based on these mean and standard deviation values, an upper band and lower band 122 with respect to an $SpO_2$ trend 124, as illustrated by the graph 226 in FIG. 4, may be calculated as follows:

Upper Band=mean+standard deviation;

Lower Band=mean−standard deviation.

Once the upper band 120 and lower band 122 have been determined, potential reciprocation peaks and nadirs may be extracted from the $SpO_2$ trend 124 using the upper band 120 and the lower band 124. Indeed, a potential peak may be identified as the highest $SpO_2$ point in a trend segment which is entirely above the upper band 120. Similarly, a potential nadir may be identified as the lowest $SpO_2$ point in a trend segment that is entirely below the lower band 122. In other words, peaks identified by the RD feature 102 may be at least one standard deviation above the rolling mean, and nadirs identified by the RD feature 102 may be at least one standard deviation below the mean. If there is more than one minimum value below the lower band 122, the last (or most recent) trend point may be identified as a nadir. If more than one maximum value is above the upper band 120, the point identified as a peak may depend on where it is in relation to the nadir. For example, regarding potential peaks that occur prior to a nadir (e.g., fall peaks) the most recent maximum trend point may be used. In contrast, for peaks that occur subsequent to a nadir (e.g., rise peaks), the first maximum point may be used. In the example trend data represented in FIG. 4, a peak and nadir is detected approximately every 30-60 seconds.

In one embodiment, a window size for calculating the mean and standard deviation may be set based on historical values (e.g., average duration of a set number of previous reciprocations). For example, in one embodiment, a window size for calculating the mean and standard deviation may be set to the average duration of all qualified reciprocations in the last 6 minutes divided by 2. In another embodiment, an adaptive window method may be utilized wherein the window size may be initially set to 12 seconds and then increased as the length of qualified reciprocations increases. This may be done in anticipation of larger reciprocations because reciprocations that occur next to each other tend to be of similar shape and size. If the window remained at 12 seconds, it could potentially be too short for larger reciprocations and may prematurely detect peaks and nadirs. The following equation or calculation is representative of a window size determination, wherein the output of the filter is inclusively limited to 12-36 seconds, and the equation is executed each time a new reciprocation is qualified:

If no qualified reciprocations in the last 6 minutes:

Window Size=12 (initial value)

else:

RecipDur=½*current qualified recip duration+½*previous RecipDur

Window Size=bound(RecipDur,12,36).

With regard to $SpO_2$ signals that are essentially flat, the dynamic window method may fail to find the three points (i.e., a fall peak, a rise peak, and a nadir) utilized to identify a potential reciprocation. Therefore, the RD feature 102 may limit the amount of time that the dynamic window method can search for a potential reciprocation. For example, if no reciprocations are found in 240 seconds plus the current adaptive window size, the algorithm of the RD feature 102 may timeout and begin to look for potential reciprocations at the current $SpO_2$ trend point and later. The net effect of this may be that the RD feature 102 detects potential reciprocations less than 240 seconds long.

Once potential peaks and nadirs are found using the RD feature 102, the RQ feature 104 may pass the potential reciprocations through one or more qualification stages to determine if a related event is caused by ventilatory instability. A first qualification stage may include checking reciprocation metrics against a set of limits (e.g., predetermined hard limits). A second qualification stage may include a linear qualification function. In accordance with present embodiments, a reciprocation may be required to pass through both stages in order to be qualified.

As an example, in a first qualification stage, which may include a limit-based qualification, four metrics may be calculated for each potential reciprocation and compared to a set of limits. Any reciprocation with a metric that falls outside of these limits may be disqualified. The limits may be based on empirical data. For example, in some embodiments, the limits may be selected by calculating the metrics for potential reciprocations from sleep lab data where ventilatory instability is known to be present, and then comparing the results to metrics from motion and breathe-down studies. The limits may then be refined to filter out true positives.

The metrics referred to above may include fall slope, magnitude, slope ratio, and path length ratio. With regard to fall slope, it may be desirable to limit the maximum fall slope to filter out high frequency artifact in the $SpO_2$ trend, and limit the minimum fall slope to ensure that slow $SpO_2$ changes are not qualified as reciprocations. Regarding magnitude, limits may be placed on the minimum magnitude because of difficulties associated with deciphering the difference between ventilatory instability reciprocations and artifact reciprocations as the reciprocation size decreases, and on the maximum magnitude to avoid false positives associated with sever artifact (e.g., brief changes of more than 35% $SpO_2$ that are unrelated to actual ventilatory instability). The slope ratio may be limited to indirectly limit the rise slope for the same reasons as the fall slope is limited and because ventilatory instability patterns essentially always have a desaturation rate that is slower than the resaturation (or recovery) rate. The path length ratio may be defined as Path Length/((Fall Peak−Nadir)+(Rise Peak−Nadir)), where Path Length=Σ|Current $SpO_2$ Value−Previous $SpO_2$ value| for all $SpO_2$ values in a reciprocation, and the maximum path length ratio may be limited to limit the maximum standard deviation of the reciprocation, which limits high frequency artifact. The following table (Table I) lists the above-identified metrics along with their associated equations and the limits used in accordance with one embodiment:

TABLE I

| Metric | Equation | Minimum | Maximum |
|---|---|---|---|
| Fall Slope | (Nadir − Fall Peak)/Time between Fall Peak and Nadir | −1.6 (Fast Response Mode) −1 (Normal Response Mode) | −0.08 (Fast Response Mode) −0.05 (Normal Response Mode) |
| Magnitude | Max(Rise Peak, Fall Peak) − Nadir | 3 | 35 |
| Slope Ratio | |Fall Slope/Rise Slope| | 0.05 | 1.75 |
| Path Length Ratio | Path Length = Σ|Current SpO2 Value − Previous SpO2 Value| for all SpO2 values in a Reciprocation. Path Length Ratio = Path Length/((Fall Peak − Nadir) + (Rise Peak − Nadir)) | N/A | 2 |

As indicated in Table I above, an oximetry algorithm in accordance with present embodiments may operate in two response modes: Normal Response Mode or Fast Response Mode. The selected setting may change the $SpO_2$ filtering performed by the oximetry algorithm, which in turn can cause changes in $SpO_2$ patterns. Therefore a saturation pattern detection feature may also accept a response mode so that it can account for the different $SpO_2$ filtering. Table I indicates values associated with both types of response mode with regard to the Fall Slope values.

A second qualification stage of the RQ feature 204 may utilize a object reciprocation qualification feature. Specifically, the second qualification stage may utilize a linear qualification function based on ease of implementation, efficiency, and ease of optimization. The equation may be determined by performing a least squares analysis. For example, such an analysis may be performed with MATLAB®. The inputs to the equation may include the set of metrics described below. The output may be optimized to a maximum value for patterns where ventilatory instability is known to be present. The equation may be optimized to output smaller values (e.g., 0) for other data sets where potential false positive reciprocations are abundant.

To simplify optimization, the equation may be factored into manageable sub-equations. For example, the equation may be factored into sub-equation 1, sub-equation D, and sub-equation 2, as will be discussed below. The output of each sub-equation may then be substituted into the qualification function to generate an output. The outputs from each of the sub-equations may not be utilized to determine whether a reciprocation is qualified in accordance with present embodiments. Rather, an output from a full qualification function may be utilized to qualify a reciprocation. It should be noted that the equations set forth in the following paragraphs describe one set of constants. However, separate sets of constants may be used based on the selected response mode. For example, a first set of constants may be used for the Normal Response Mode and a second set of constants may be used for the Fast Response Mode.

Preprocessing may be utilized in accordance with present embodiments to prevent overflow for each part of the qualification function. The tables (Tables II-VII) discussed below, which relate to specific components of the qualification function may demonstrate this overflow prevention. Each row in a table contains the maximum value of term which is equal to the maximum value of the input variable multiplied by the constant, wherein the term "maximum" may refer to the largest possible absolute value of a given input. Each row in a table contains the maximum intermediate sum of the current term and all previous terms. For example, a second row may contain the maximum output for the second term calculated, as well as the maximum sum of terms 1 and 2. It should be noted that the order of the row may match the order that the terms are calculated by the RQ feature 204. Further, it should be noted that in the tables for each sub-equation below, equations may be calculated using temporary signed 32-bit integers, and, thus, for each row in a table where the current term or intermediate term sum exceeds 2147483647 or is less than −2147483647 then an overflow/underflow condition may occur.

A first sub-equation, sub-equation 1, may use metrics from a single reciprocation. For example, sub-equation 1 may be represented as follows:

Eq1Score=SlopeRatio*SrCf+PeakDiff*PdCf+ FallSlope*FsCf+PathRatio*PrCf+Eq1Offset, where SrCf, PdCf, FsCf, PrCf, and Eq1Offset may be selected using least squares analysis (e.g., using MATLAB®). PeakDiff may be defined as equal to |Recip Fall Peak−Recip Rise Peak|. It should be noted that PeakDiff is typically not considered in isolation but in combination with other metrics to facilitate separation. For example, a true positive reciprocation which meets other criteria but has a high peak difference could be an incomplete recovery. That is, a patient's $SpO_2$ may drop from a baseline to a certain nadir value, but then fail to subsequently recover to the baseline. However, when used in combination with other metrics in the equation, PeakDiff may facilitate separation of two classifications, as large peak differences are more abundant in false positive data sets.

With regard to sub-equation 1, the tables (Tables II and III) set forth below demonstrate that the inputs may be preprocessed to prevent overflow. Further, the tables set forth below include exemplary limits that may be utilized in sub-equation 1 in accordance with present embodiments. It should be noted that Table II includes Fast Response Mode constants and Table III includes Normal Response Mode constants.

TABLE II

| Term | Variable Type | Maximum Variable Value (a) | Variable Preprocessing | Constant Value (b) (Fast Mode) | Maximum Term Value (a * b) | Maximum Intermediate Sum (Sum of all previous rows) | Overflow |
|---|---|---|---|---|---|---|---|
| PeakDiff*PdCf | U8 | 100 | None. This value may not exceed 100 since the maximum SpO$_2$ value accepted is 100 | −29282 | −2928200 | −2928200 | NO |
| SlopeRatio*SrCf | U8 | 255 | None | −1534 | −391170 | −3319370 | NO |
| FallSlope*FsCf | S16 | −32768 | None | −19 | 622592 | −2696778 | NO |
| PathRatio*PrCf | U16 | 65535 | None | −7982 | −523100370 | −525797148 | NO |
| Eq1Offset | N/A | N/A | N/A | 809250 | 809250 | −524987898 | NO |

TABLE III

| Term | Variable Type | Maximum Variable Value (a) | Variable Preprocessing | Constant Value (b) (Normal Mode) | Maximum Term Value (a * b) | Maximum Intermediate Sum (Sum of all previous rows) | Overflow |
|---|---|---|---|---|---|---|---|
| PeakDiff*PdCf | U8 | 100 | None. This value may not exceed 100 since the maximum SpO$_2$ value accepted is 100 | −33311 | −3331100 | −3331100 | NO |
| SlopeRatio*SrCf | U8 | 255 | None | −2151 | −548505 | −3879605 | NO |
| FallSlope*FsCf | S16 | −32768 | None | −706 | 23134208 | 19254603 | NO |
| PathRatio*PrCf | U16 | 65535 | None | −6178 | −404875230 | −385620627 | NO |
| Eq1Offset | N/A | N/A | N/A | 576330 | 576330 | −385044297 | NO |

A second sub-equation, sub-equation D, may correspond to a difference between two consecutive reciprocations which have passed the hard limit qualifications checks, wherein consecutive reciprocations include two reciprocations that are separated by less than a defined time span. For example, consecutive reciprocations may be defined as two reciprocations that are less than 120 seconds apart. The concept behind sub-equation D may be that ventilatory instability tends to be a relatively consistent event, with little change from one reciprocation to the next. Artifact generally has a different signature and tends to be more random with greater variation among reciprocations. For example, the following equation may represent sub-equation D:

$$EqD = SlopeRatioDiff*SrDCf + DurationDiff*DDCf + NadirDiff*NdCf + PathLengthRatioDiff*PrDCf\_EqDOffset,$$

where, SrDCf, DDCf, NdCf, PrDCf, and EqDOffset may be selected using least squares analysis (e.g., using MATLAB®). With regard to other variables in sub-equation D, SlopeRatioDiff may be defined as |Current Recip Slope Ratio−Slope Ratio of last qualified Recip|; DurationDiff may be defined as |Current Recip Duration−Duration of last qualified Recip|; NadirDiff may be defined as |Current Recip Nadir−Nadir value of last qualified Recip|; and PathLengthRatioDiff may be defined as |Current Recip Path Length Ratio−Path Length Ratio of last qualified Recip|.

With regard to sub-equation D, the tables (Tables IV and V) set forth below demonstrate that the inputs may be preprocessed to prevent overflow. Further, the tables set forth below include exemplary limits that may be utilized in sub-equation D in accordance with present embodiments. It should be noted that Table IV includes Fast Response Mode constants and Table V includes Normal Response Mode constants.

TABLE IV

| Term | Variable Type | Maximum Variable Value (a) | Variable Preprocessing | Constant Value (b) (Fast Mode) | Maximum Term Value (a * b) | Maximum Intermediate Sum (Sum of all previous rows) | Overflow |
|---|---|---|---|---|---|---|---|
| EqDOffset | N/A | N/A | N/A | 885030 | 885030 | 885030 | NO |
| SlopeRatioDiff* SrDCf | U8 | 255 | None | −2809 | −716295 | 168735 | NO |
| DurationDiff * DDCf | U16 | 240 | The Recip detection module recips less than or equal to 240 seconds long | −2960 | −710400 | −541665 | NO |
| NadirDiff* NdCf | U8 | 100 | This value may not exceed 100 since the maximum SpO2 value accepted in 100 | −13237 | −1323700 | −1865365 | NO |
| PathLength RatioDiff *PrDCf | U16 | 65535 | None | 7809 | −511762815 | −513628180 | NO |

TABLE V

| Term | Variable Type | Maximum Variable Value (a) | Variable Preprocessing | Constant Value (b) (Normal Mode) | Maximum Term Value (a * b) | Maximum Intermediate Sum (Sum of all previous rows) | Overflow |
|---|---|---|---|---|---|---|---|
| EqDOffset | N/A | N/A | N/A | 847650 | 847650 | 847650 | NO |
| SlopeRatioDiff *SrDCf | U8 | 255 | None | −2629 | −670395 | 177255 | NO |
| DurationDiff* DDCf | U16 | 240 | The Recip detection module may only detect recips less than or equal to 240 seconds long | −4282 | −1027680 | −850425 | NO |
| NadirDiff* NdCf | U8 | 100 | This value may not exceed 100 since the maximum SpO2 value accepted in 100 | −11705 | −1170500 | −2020925 | NO |
| PathLengthRatio Diff *PrDCf | U16 | 65535 | None | 7844 | −514056540 | −516077465 | NO |

A third sub-equation, sub-equation 2, may combine the output of sub-equation D with the output of sub-equation 1 for a reciprocation (e.g., a current reciprocation) and a previous reciprocation. For example, the following equation may represent sub-equation 2:

Eq2Score=EqDScore*DCf+
    Eq1ScoreCurrent*CurrEq1Cf+
    Eq1ScorePrev*PrevEq1Cf, where DCf, N1Cf, PrevEq1Cf, and Eq2Offset may be selected using least squares analysis (e.g., using MATLAB®). With regard to other variables in sub-equation 2, EqDScore may be described as the output of sub-equation D; Eq1ScoreCurrent may be described as the output of sub-equation 1 for a current reciprocation; and Eq1ScorePrev may be described as the output of sub-equation 1 for the reciprocation previous to the current reciprocation.

With regard to sub-equation 2, the tables (Tables VI and VII) set forth below demonstrate that the inputs may be preprocessed to prevent overflow. Further, the tables set forth below include exemplary limits that may be utilized in sub-equation 2 in accordance with present embodiments. It should be noted that Table VI includes Fast Response Mode constants and Table VII includes Normal Response Mode constants.

TABLE VI

| Term | Variable Type | Maximum Variable Value (a) | Variable Preprocessing | Constant Value (b) (Fast Mode) | Maximum Term Value(a * b) | Maximum Intermediate Sum (Sum of all previous rows) | Overflow |
|---|---|---|---|---|---|---|---|
| Eq2Offset | N/A | N/A | N/A | −2038000 | −203800 | −203800 | NO |
| EqDScore * DCf | S32 | −501590 | The largest output for Sub-equation D may be −513628100 (see Table IV). The input value may be scaled by dividing the value by 1024. | 529 | −265341110 | −265544910 | NO |

TABLE VI-continued

| Term | Variable Type | Maximum Variable Value (a) | Variable Preprocessing | Constant Value (b) (Fast Mode) | Maximum Term Value(a * b) | Maximum Intermediate Sum (Sum of all previous rows) | Overflow |
|---|---|---|---|---|---|---|---|
| Eq1ScorePrev * PrevEq1Cf | S32 | −512683 | Therefore the largest input value may be −501590 The largest output for sub-equation 1 may be −524987898 (see Table II). The input value may be scaled by dividing the value by 1024. Therefore the largest input value may be −512683 | 333 | −170723439 | −436268349 | NO |
| Eq1ScoreCurrent * CurrEq1Cf | S32 | −512683 | Same as previous row | 617 | −316325411 | −752593760 | NO |

TABLE VII

| Term | Variable Type | Maximum Variable Value (a) | Variable Preprocessing | Constant Value (b) (Normal Mode) | Maximum Term Value(a * b) | Maximum Maximum Sum (Sum of all previous rows) | Intermediate Overflow |
|---|---|---|---|---|---|---|---|
| Eq2Offset | N/A | N/A | N/A | −194550 | −194550 | −194550 | NO |
| EqDScore * DCf | S32 | −503981 | The largest output for Sub-equation D may be −516077465 (see Table V). The input value may be scaled by dividing the value by 1024. Therefore the largest input value may be −503981 | 532 | −268117892 | −268312442 | NO |
| Eq1ScorePrev * PrevEq1Cf | S32 | −376000 | The largest output for sub-equation 1 may be −385024297 (see Table III). The input value may be scaled by dividing the value by 1024. Therefore the largest input value may be −376000 | 496 | −186496000 | −454808442 | NO |
| Eq1ScoreCurrent * CurrEq1Cf | S32 | −376000 | Same as previous row | 406 | −152656000 | −607464442 | NO |

A qualification function may utilize the output of each of the equations discussed above (i.e., sub-equation 1, sub-equation D, and sub-equation 2) to facilitate qualification and/or rejection of a potential reciprocation. For example, the output of the qualification function may be filtered with an IIR filter, and the filtered output of the qualification function may be used to qualify or reject a reciprocation. An equation for an unfiltered qualification function output in accordance with present embodiments is set forth below:

QFUnfiltered=Eq1Score*SingleRecipWt*Eq2Cf+
N2Score*MultipleRecipWt*Eq2Cf+
NConsecRecip*ConsecCf+RecipMax*MaxCf+
Artifact %*ArtCf+QFOffset, where Eq2Cf, ConsecCf, MaxCf, ArtCf, and QFOffset may be selected using least squares analysis (e.g., using MATLAB®), and, as indicated above, Eq1Score may be defined as the output of sub-equation 1.

Other metrics in the unfiltered qualification function include SingleRecipWt, MultipleRecipWt, NConsecRecip, RecipMax, and Artifact %. With regard to SingleRecipWt and MultipleRecipWt, when there are two or more consecutive qualified reciprocations (e.g., qualified reciprocations that are less than 120 seconds apart) present, SingleRecipWt may equal 0 and MultipleRecipWt may equal 1. However, when only a single reciprocation is present, SingleRecipWt may equal 1 and MultipleRecipWt may equal 0.

NConseRecip, which may be defined as equal to max (NConsecRecip',QFConsecMax), may include a count of the number of consecutive reciprocations (e.g., reciprocations that are less than or equal to 120 seconds apart) that have passed the hard limit checks. The value for NConsecRecip may be reset to 0 whenever a gap between any two partially qualified reciprocations exceeds 120 seconds. This may be based on the fact that ventilatory instability is a relatively long lasting event as compared to artifact. Therefore, as more reciprocations pass the hard limit checks, the qualification function may begin qualifying reciprocations that were previously considered marginal. However, to guard against a situation where something is causing a longer term artifact event (e.g., interference from nearby equipment), the value may be clipped to a maximum value to limit the metrics influence on the qualification function output.

RecipMax, which may be defined as equal to max(Fall Peak, Rise Peak), may facilitate making decisions about marginal reciprocations. Indeed, marginal reciprocations with higher maximum $SpO_2$ values may be more likely to get qualified than marginal reciprocations with lower $SpO_2$ values. It should be noted that this metric works in tandem with the NConsecRecip metric, and multiple marginal reciprocations with lower maximum $SpO_2$ values may eventually, over a long period of time, get qualified due to the NConsecRecip metric.

The metric Artifact % may be defined as an artifact percentage that is equal to 100*Total Artifact Count/Recip Duration, where Total Artifact Count is the number of times and artifact flag was set during the reciprocation. Present embodiments may include many metrics and equations that are used to set the artifact flag. Because of this it is a generally reliable indication of the amount of artifact present in the oximetry system as a whole. Marginal reciprocations with a high Artifact % are less likely to be qualified than marginal reciprocations with a low (or 0) artifact percentage.

A last component of the qualification function may include an infinite impulse response (IIR) filter that includes coefficients that may be tuned manually using a tool (e.g., a spreadsheet) that models algorithm performance. The filtered qualification function may be represented by the following equation, which includes different constants for different modes (e.g., Fast Response Mode and Normal Response Mode):

QFFiltered=SingleRecipWt*QFUnfiltered+
((1−a)*QFUnfiltered+a*PrevQFFiltered)*MultipleRecipWt, where QFUnfiltered may be defined as the current unfiltered qualification function output; PrevQFFiltered may be defined as the previous filtered qualification function output; and where the constat "a" may be set to 0.34 for Fast Response Mode and 0.5 for Normal Response Mode.

The filtered output of the qualification function may be compared to a threshold to determine if the current reciprocation is the result of RAF or artifact. The optimum threshold may theoretically be 0.5. However, an implemented threshold may be set slightly lower to bias the output of the qualification function towards qualifying more reciprocations, which may result in additional qualification of false positives. The threshold may be lowered because, in accordance with present embodiments, a cluster determination portion of the algorithm, such as may be performed by the CD feature 106, may require a certain number (e.g., 5) of fully qualified reciprocations before an index may be calculated, and a certain number (e.g., at least 2) of consecutive qualified reciprocations (with no intervening disqualified reciprocations) within the set of fully qualified reciprocations. Since multiple reciprocations may be required, the clustering detection method may be biased toward filtering out false positives. Accordingly, the reciprocation qualification function threshold may be lowered to balance the two processes.

The CD feature 106 may be capable of performing an algorithm that maintains an internal reciprocation counter that keeps track of a number of qualified reciprocations that are currently present. When the reciprocation counter is greater than or equal to a certain value, such as 5, the clustering state may be set to "active" and the algorithm may begin calculating and reporting the detection of clusters. When clustering is not active (e.g., reciprocation count<5) the algorithm may not report the clusters.

The CD feature 106 may utilize various rules to determine the reciprocation count. For example, when the clustering state is inactive, the following rules may be observed:

1.) If the distance between qualified reciprocation exceeds 120 seconds, then the reciprocation count=0;
2.) If the current reciprocation is qualified, and the time from the start of the current reciprocation to the end of the last qualified reciprocation is <=120 seconds, then the reciprocation count=reciprocation count+1;
3.) If the current reciprocation is not qualified, then the reciprocation count=max(reciprocation count−2, 0).

Once clustering is active, it may remain active until the time between two qualified reciprocations exceeds 120 seconds. The following table (Table II) illustrates an example of how the reciprocation count rules may be applied to determine a clustering state.

TABLE VIII

| Current Reciprocation Qualified | Time Since Last Qualified Reciprocation (seconds) | Reciprocation Count | Clustering State |
|---|---|---|---|
| TRUE | N/A | 1 | INACTIVE |
| FALSE | 60 | 0 | INACTIVE |
| TRUE | N/A | 1 | INACTIVE |
| FALSE | 60 | 0 | INACTIVE |
| TRUE | N/A | 1 | INACTIVE |
| TRUE | 30 | 2 | INACTIVE |
| TRUE | 120 | 3 | INACTIVE |
| FALSE | 60 | 1 | INACTIVE |
| TRUE | 10 | 2 | INACTIVE |
| TRUE | 20 | 3 | INACTIVE |
| TRUE | 40 | 4 | INACTIVE |
| FALSE | 30 | 2 | INACTIVE |
| FALSE | 60 | 0 | INACTIVE |
| TRUE | N/A | 1 | INACTIVE |
| TRUE | 20 | 2 | INACTIVE |
| TRUE | 120 | 3 | INACTIVE |
| TRUE | 10 | 4 | INACTIVE |
| FALSE | 90 | 2 | INACTIVE |
| TRUE | 120 | 3 | INACTIVE |
| TRUE | 60 | 4 | INACTIVE |
| TRUE | 20 | 5 | ACTIVE |
| TRUE | 30 | 6 | ACTIVE |
| FALSE | 50 | 6 | ACTIVE |
| FALSE | 100 | 6 | ACTIVE |
| TRUE | 121 | 1 | INACTIVE |
| FALSE | 50 | 0 | INACTIVE |
| TRUE | N/A | 1 | INACTIVE |
| TRUE | 30 | 2 | INACTIVE |
| TRUE | 121 | 1 | INACTIVE |
| TRUE | 10 | 2 | INACTIVE |
| TRUE | 20 | 3 | INACTIVE |
| TRUE | 40 | 4 | INACTIVE |
| TRUE | 40 | 5 | ACTIVE |

In addition to cluster detection, embodiments may also include an integral alarm limit detection feature 109 that is configured to detect if the $SpO_2$ signal 34 drops below a lower limit 48. In the embodiment shown in FIG. 4, this limit 48 may be set at an SpO2 level of 85%. In other embodiments, the level may be 95%, 90%, 80%, 75%, or any other appropriate value selected by the practitioner based on the patient's condition.

The use of an absolute limit, however, may result in numerous alarms that are not necessarily informative. Accordingly, methods may be used to determine the severity of the condition and only alert the practitioner if the condition persists. For example, in an embodiment, the integral alarm limit detection feature 109 may calculate an integral 50 from the $SpO_2$ signal 34 by using a summation of the time the signal 34 may be below the lower limit 48 multiplied by the amount the signal 34 may be below the lower limit 48. Similarly, an upper limit (not shown) may also be used for calculating the integral 50. An integral alarm limit 52 may be selected for alerting a practitioner based on the value of the integral 50. In embodiments, calculation of the integral 50 may be performed by the methods detailed in U.S. Pat. No. 5,865,736 (hereinafter the '736 patent), which is hereby incorporated by reference as if fully set forth herein.

The integral alarm limit detection feature 109 and the CD feature 106 may provide reports or other indications to a user notification feature 108 that may be configured to alert a user if there is one or more of a cluster detection or integral alarm limit violation. Referring back to FIG. 2, a combined alarm limit 54 may be based on both the presence of desaturation patterns 38, or clusters 46 (e.g., clusters determined by any suitable method), and the value of the integral 50. In this embodiment, if desaturation patterns 38, or clusters 46, are present and the integral 50 reaches the value of the combined alarm limit 54 an alert may be activated. In an embodiment, the limit for the combined alarm 54 may not be directly set by a practitioner, but may instead by calculated from the value of other parameters set by the practitioner. For example, the value of the combined alarm limit 54 may be calculated using the formula given in equation 1:

$$CAL = CAS*IAL/100 \qquad \text{equation 1.}$$

In this equation, CAL may be the combined alarm limit 54, CAS may be a combined alarm sensitivity set by the user, and IAL may be the integral alarm limit 52 discussed above.

Figure 5:
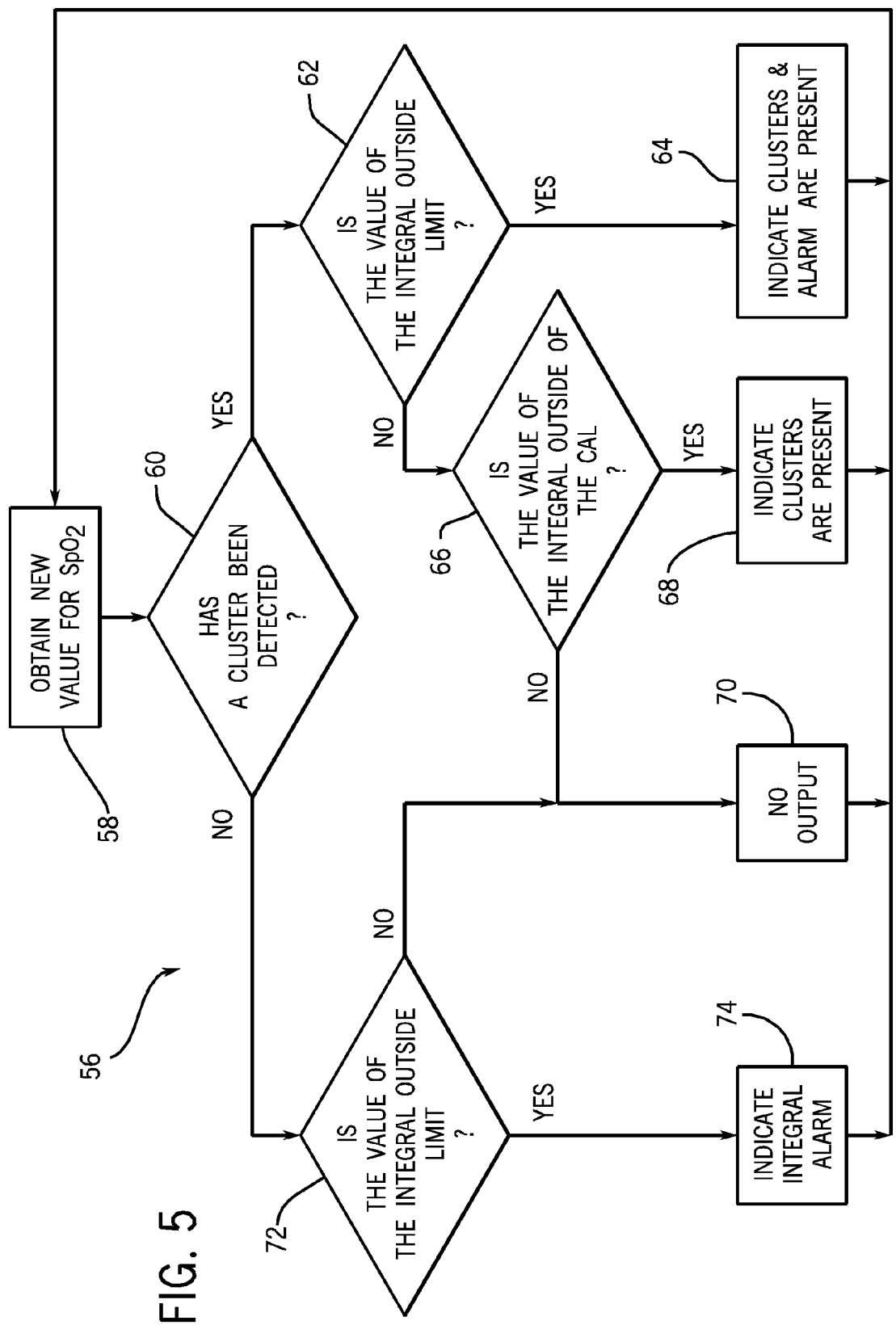
FIG. 5 is a process flow chart showing a method for alerting practitioners to the presence of certain physiological conditions, in accordance with an embodiment.

FIG. 5 is a process flow chart showing a method 56 for alerting practitioners to the presence of certain physiological conditions, in accordance with an embodiment. Referring also to FIG. 2, the method 56 of FIG. 5 starts with the collection of a new sample for the SpO$_2$ signal 34, as shown in block 58. As shown in block 60, the SpO$_2$ signal 34 may be analyzed to determine if a new cluster 46, e.g., two or more of the desaturation patterns 38 in sequence or a cluster as detected by a programmed functional unit 100, has been detected. In other embodiments, the method 56 may be configured to determine if only one of the desaturation patterns 38 may be detected. If a cluster 46 has been detected, the method 56 proceeds to block 62, to determine if the integral 50 has reached the integral alarm limit 52. If so, as shown in block 64, the method 56 may inform a practitioner that the integral alarm limit 52 has been reached and clusters 46 are present in the SpO$_2$ signal 34. The method 56 may then return to block 58 to collect the next SpO$_2$ sample in the SpO$_2$ signal 34.

If no integral alarm condition has been detected in block 62, the method may determine if the combined alarm limit 54 has been reached by the integral 50, as shown in block 66. The combined alarm limit 54 may be calculated using the method discussed with respect to equation 1. Further, the combined alarm limit 54 may be set to zero, which would inform the user of the presence of clusters 46, even if the value for the integral 50 was zero. If the combined alarm limit 54 has been reached, the method 56 may inform a practitioner that clusters 46 are present, as shown in block 68. If the combined alarm limit 54 has not been reached, the method 56 may activate no alerts, as shown in block 70. After either blocks 68 or 70, the method 56 may return to block 58 to collect the next SpO$_2$ sample in the SpO$_2$ signal 34.

If a cluster 46 may be not detected in block 60, the method 56 may still determine if the integral 50 has reached the integral alarm limit 52, as shown in block 72. If the integral 50 has not reached the integral alarm limit 52, no alarm may be activated, as shown in block 70. However, if the integral 50 has reached the integral alarm limit 52, the method 56 may inform a practitioner that the integral alarm limit 52 has been reached, as shown in block 74. After activating the alert, the method 56 may return to block 58 to collect the next SpO$_2$ sample in the SpO$_2$ signal 34.

The operation of an embodiment of the method 56 discussed with respect to FIG. 5 may be illustrated by the charts shown in FIGS. 6-9. In each of these charts, as in FIG. 2, the SpO$_2$ signal 34 may be plotted against the percent blood oxygen saturation level (SpO$_2$) on the left vertical axis 36 and the time, in seconds, on the horizontal axis 38. The horizontal line at a value of 85% on the SpO2 axis 36 represents the lower limit 48 that may be used for controlling alarms or in the calculation of the integral 50. The value for the integral 50 may be plotted on each chart, showing the response of the method under the conditions described. An alarm condition indicator line 76 may be used to visually indicate the presence of an alarm condition, for example, when the value of the integral 50 exceeds the combined alarm limit 54 or the integral alarm limit 52. In embodiments, other indicators of the alarm status may be used in addition to, or in place of, the alarm condition indicator line 76. For example, audible alerts on the local unit 10 or on devices attached to a local area network 28, as discussed with respect to FIG. 1, may be activated.

Figure 6:
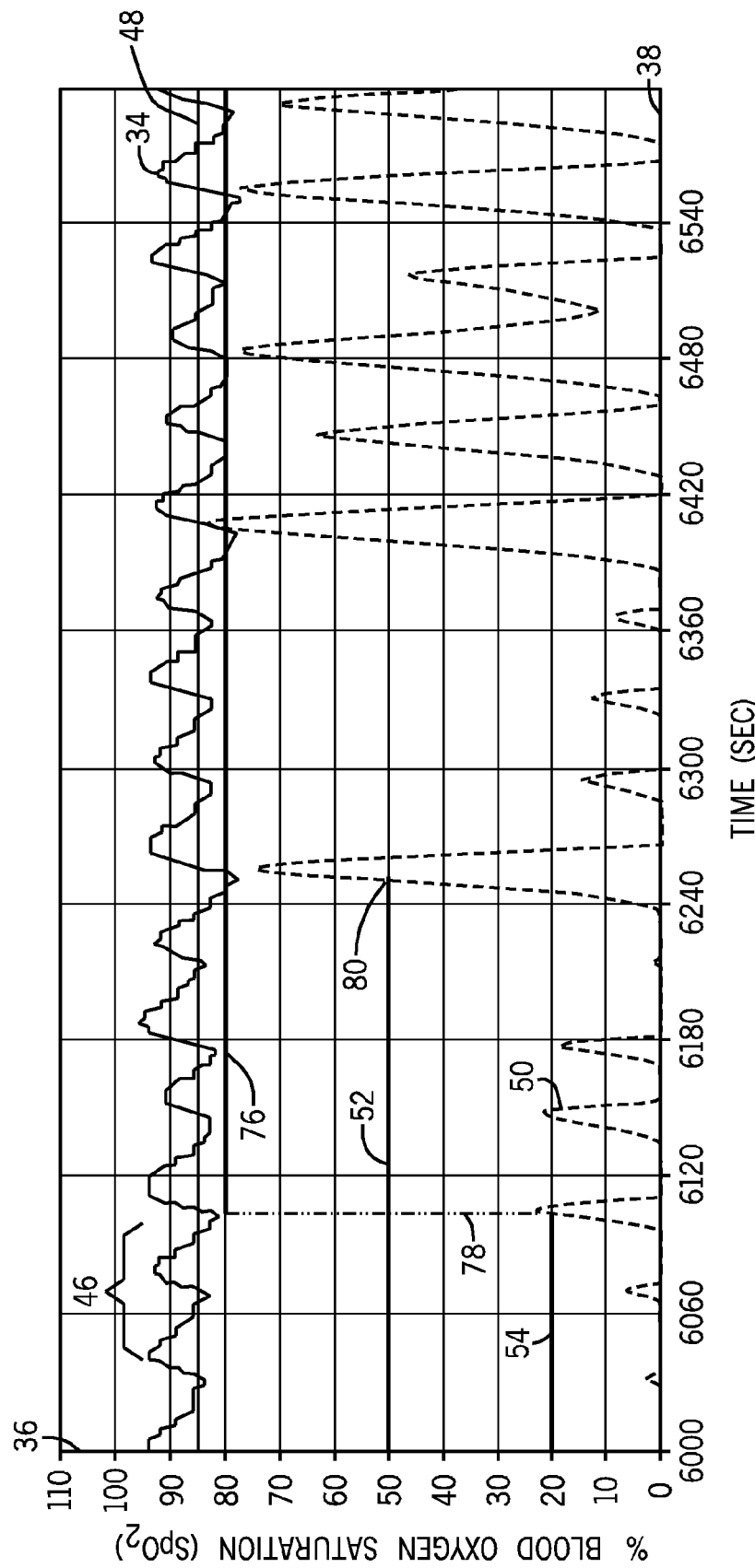
FIG. 6 is a chart useful in explaining the operation of the method of FIG. 5 to alert a practitioner to the presence of desaturation patterns when an integral representing blood oxygen saturation crosses a combined alarm limit, in accordance with an embodiment.

FIG. 6 is a chart of an SpO$_2$ signal 34 that may illustrate the operation of an embodiment. In this example, a practitioner may wish to be informed of the presence of clusters before the value of the integral 50 has reached the integral alarm limit 52, but does not want to be informed of short duration desaturation events. To achieve this, the practitioner may set the integral alarm limit 52 to 50 and the combined alarm sensitivity to 40%. Using equation 1, this provides a value of 20% for the combined alarm limit 54. The value for the integral 50 reaches the combined alarm limit 54 at about 6105 seconds, as indicated by reference numeral 78, which may result in the presence of the alarm condition indicator line 76. Although the value of the integral 50 later reaches the integral alarm limit 52, as indicated by reference numeral 80, the method 56 has already activated an alarm condition and no further alarm may be activated. However, in other embodiments, a further alarm condition may be activated to indicate the possible presence of a more severe condition. This could be performed, for example, by changing the color of the alarm condition indicator line 78 from yellow to red, by pulsing an audible alarm, or any combination thereof.

Figure 7:
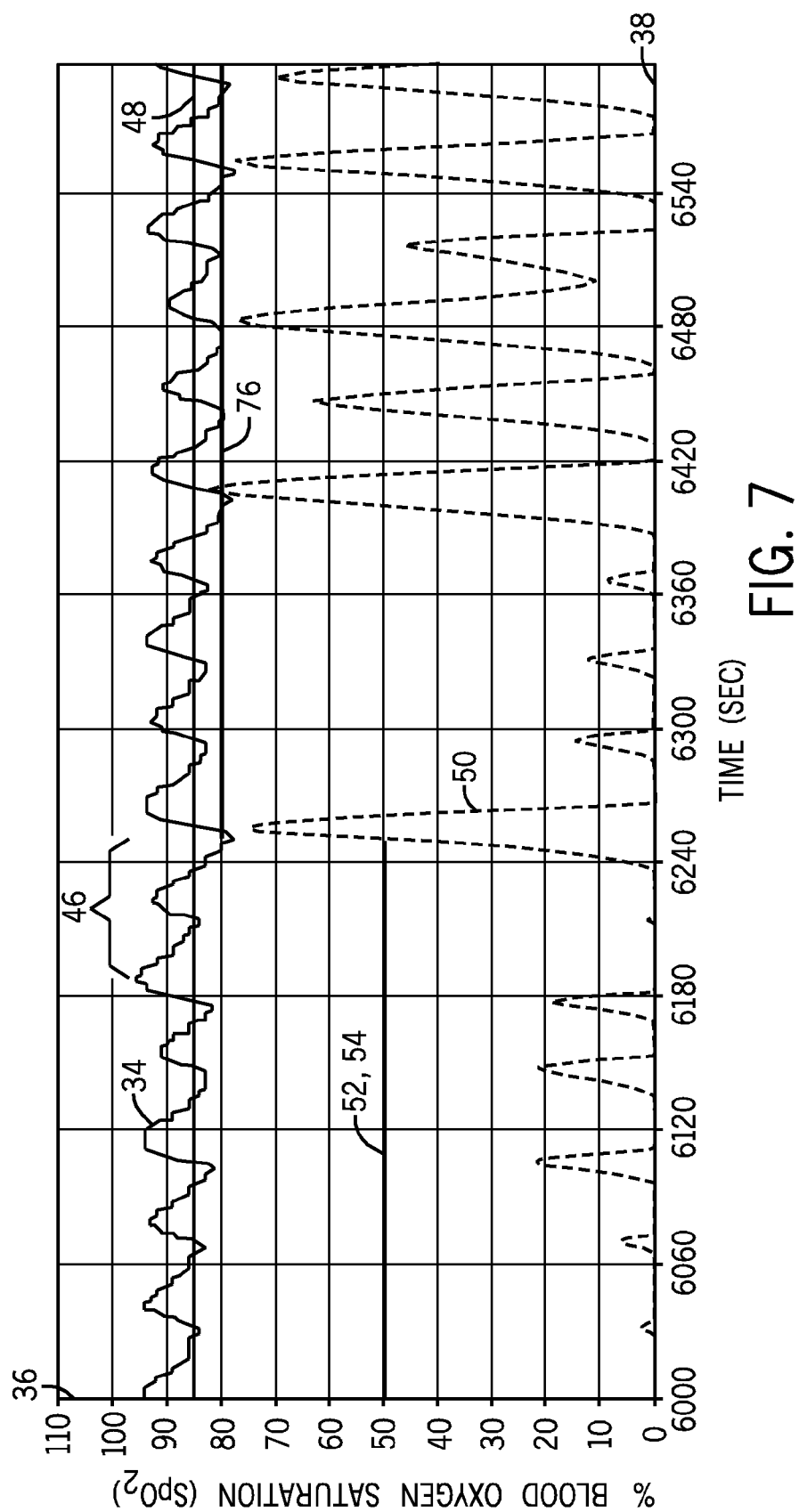
FIG. 7 is a chart useful in explaining the performance of the method of FIG. 5 when a user has chosen to ignore desaturation patterns unless an integral representing blood oxygen saturation crosses an integral alarm limit, in accordance with an embodiment.

FIG. 7 is another chart of the SpO$_2$ signal 34 that may illustrate the operation of an embodiment. A practitioner may not wish to be informed of the presence of clusters 46 unless the integral 50 has reached the integral alarm limit 52. To achieve this, the practitioner may set the combined alarm sensitivity to 100%. If the integral alarm limit 52 is set to 50, equation 1 would provide a combined alarm limit 54 that is at 50%. As shown in FIG. 7, when the value for the integral 50 reaches 50%, both the integral alarm limit 52 and the combined alarm limit 54 are simultaneously activated, resulting in the presence of the alarm condition indicator line 76.

Figure 8:
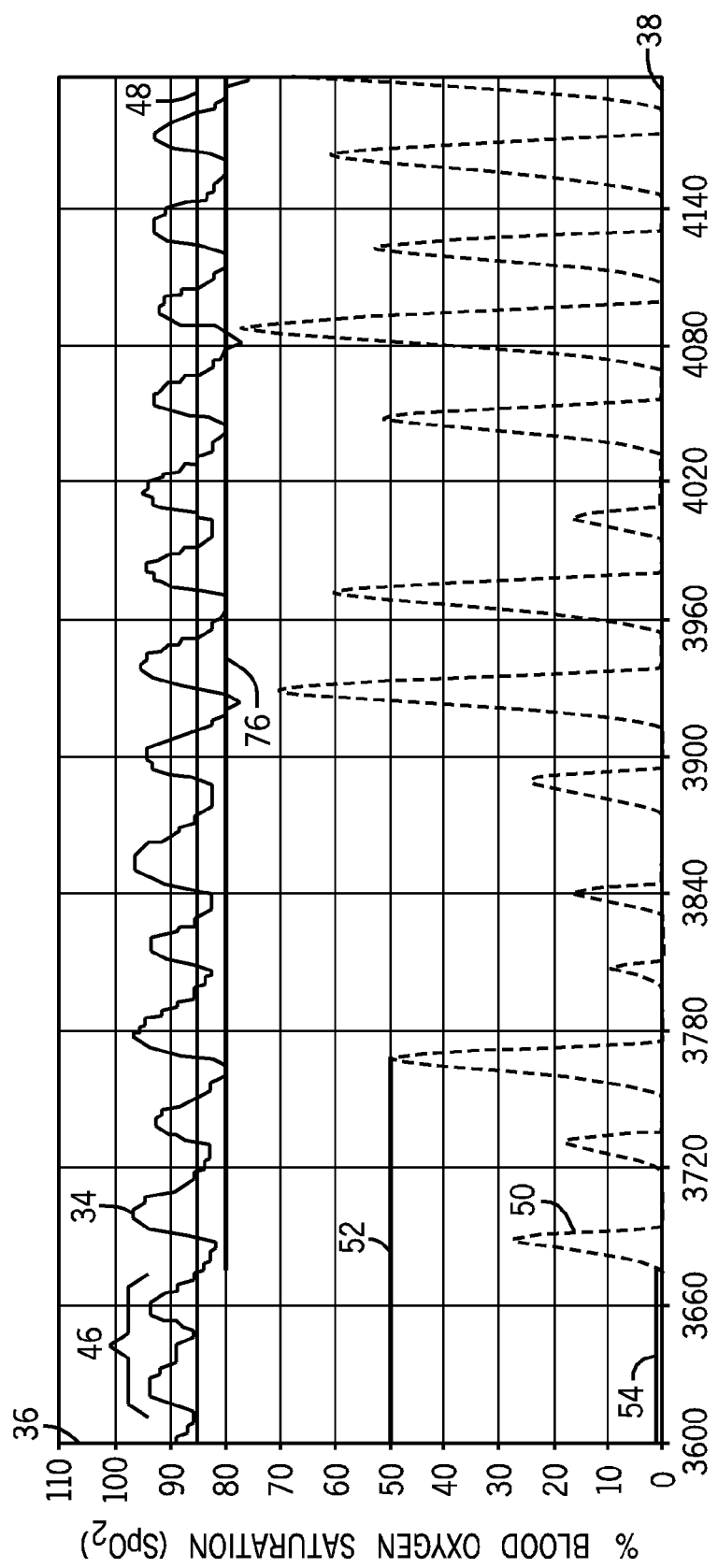
FIG. 8 is a chart useful in explaining the performance of the method of FIG. 5 when a user has chosen to be alerted to the presence of desaturation patterns whenever the $SpO_2$ signal is below a lower limit, in accordance with an embodiment.

FIG. 8 is another chart of the SpO$_2$ signal 34 that may illustrate the operation of an embodiment. A practitioner may wish to be informed anytime there are clusters 46 present in the SpO$_2$ signal 34 and the SpO$_2$ value drops below the lower limit 48. To achieve this, the practitioner may set the combined alarm sensitivity to 1%. If the value for the integral alarm limit 52 is set to 50, equation 1 would provide a value of 0.5% for the combined alarm limit 54. Accordingly, the method 56 would display the alarm condition indicator line 76 if clusters 46 are present and the value of the integral 50 is greater than 0.5%. Thus, the alarm condition would be indicated well before the value of the integral 50 reached the integral alarm limit 52.

Figure 9:
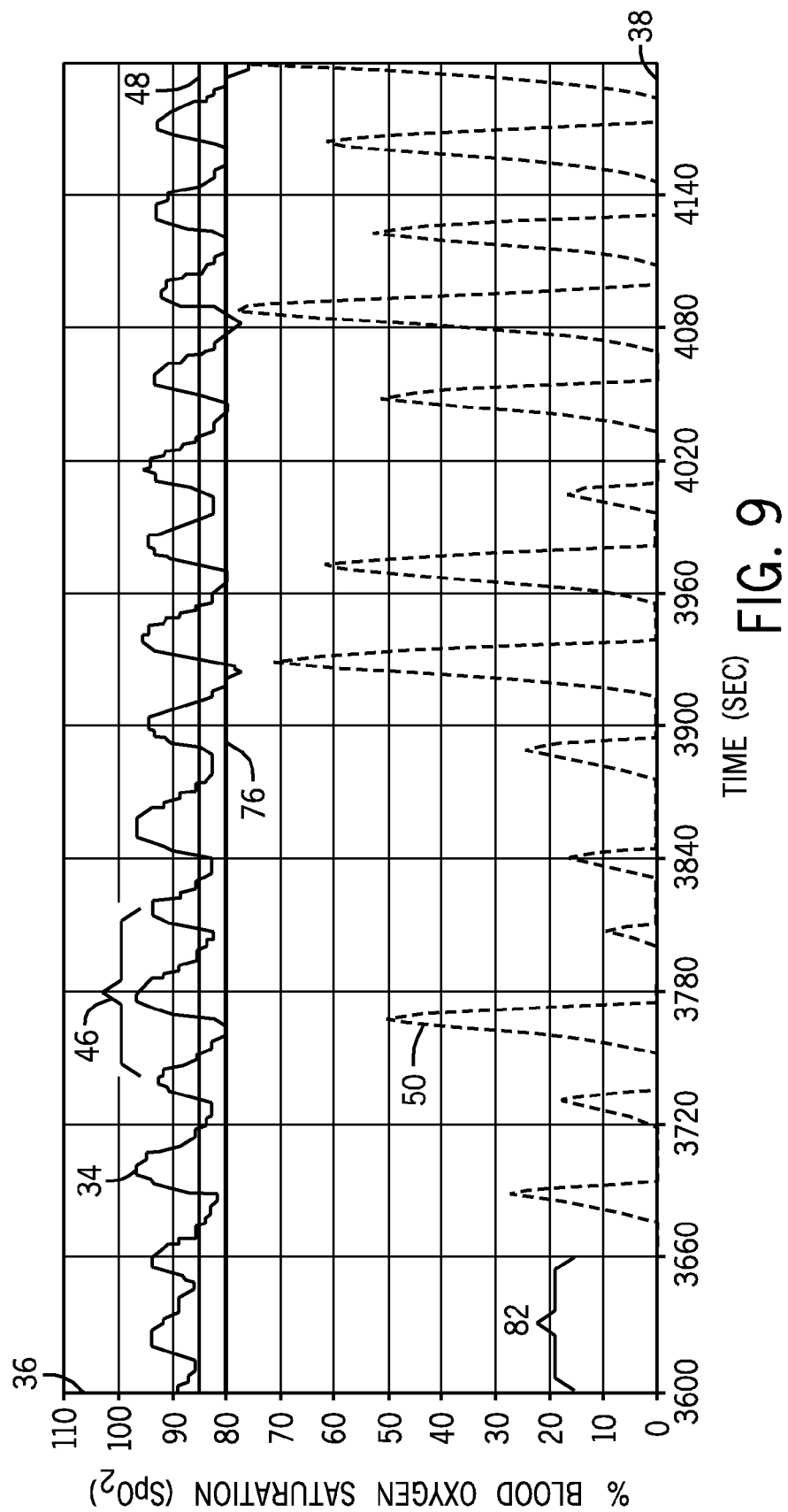
FIG. 9 is a chart useful in explaining the performance of the method of FIG. 5 when a user has chosen to be alerted to the presence of desaturation patterns under any blood oxygen condition, in accordance with an embodiment.

FIG. 9 is another chart of the $SpO_2$ signal 34 that may illustrate the operation of an embodiment. In this example, a practitioner may wish to be informed of the presence of clusters 46 anytime they are present, regardless of the value of the integral 50. Accordingly, the practitioner may set the value for the combined alarm sensitivity to 0%. Thus, the alarm conditioner indicator line 76 is present anytime clusters 46 are present, including during periods in which the value of the integral 50 may be zero, as indicated by reference numeral 82.

While the disclosure is suitable to various modifications and alternative forms, embodiments have been shown by way of example in the drawings and have been described in detail herein. However, it should be understood that the disclosure is not intended to be limited to the particular forms disclosed. Rather, the disclosure is intended to encompass all modifications, equivalents, and alternatives falling within the spirit and scope of this disclosure as defined by the following appended claims.

What is claimed is:

1. A method of evaluating a condition of a patient based on blood oxygen saturation data, the method comprising:
   monitoring a patient with a sensor to produce a signal comprising a sequence of numerical values for a physiological parameter over a time period;
   analyzing the signal with a processor of a patient monitor to determine a presence of one or more oxygen desaturation patterns;
   determining, with the processor, a value for an integral of the signal if the signal is outside of a predetermined range or threshold;
   determining, with the processor, whether the signal is indicative of sleep apnea or another type of desaturation event based at least in part upon both the presence of the one or more oxygen desaturation patterns and the value of the integral;
   providing, with the processor, an indication of sleep apnea based at least in part upon the determination that the signal is indicative of sleep apnea; and
   providing, with the processor, an indication of another type of desaturation event based at least in part upon the determination that the signal is indicative of another type of desaturation event.

2. The method of claim 1, wherein determining the value of the integral comprises accumulating, with the processor, a product of time and a difference between the signal and a threshold value.

3. The method of claim 1, comprising determining, with the processor, if a combined alarm limit has been violated based at least in part on the presence of the one or more oxygen desaturation patterns and the value of the integral, wherein the value of the integral is compared to the combined alarm limit when one or more oxygen desaturation patterns are present.

4. The method of claim 3, comprising providing, with the processor, the indication of sleep apnea when a cluster of the oxygen desaturation patterns is present and the value of the integral is greater than the value of the combined alarm limit.

5. The method of claim 1, comprising providing, with the processor, the indication of sleep apnea when a cluster of the oxygen desaturation patterns is present and the value of the integral is greater than a value of an integral alarm limit.

6. The method of claim 1, comprising providing, with the processor, the indication of sleep apnea when the value of the integral is greater than an integral alarm limit.

7. The method of claim 1, wherein providing, with the processor, the indication of sleep apnea comprises providing the indication of sleep apnea on a visual display on the patient monitor.

8. The method of claim 1, wherein providing the indication of sleep apnea comprises providing the indication of sleep apnea as an audible alarm signal on the patient monitor.

9. The method of claim 1, wherein providing the indication of sleep apnea comprises providing the indication of sleep apnea as a message to a device on a local area network.

10. A method of evaluating a condition of a patient based on blood oxygen saturation data, the method comprising:
    analyzing, with a processor of a patient monitor, a physiological signal to determine a presence of one or more oxygen desaturation patterns;
    determining, with the processor, a value for an integral if the physiological signal is outside of a range or threshold;
    providing, with the processor, an indication of sleep apnea based at least in part upon both the presence of the one or more oxygen desaturation patterns and a determination that the value of the integral is greater than a first integral threshold; and
    providing, with the processor, an indication of another type of desaturation event based at least in part upon both an absence of the one or more oxygen desaturation patterns and a determination that the value of the integral is greater than a second integral threshold.

11. The method of claim 10, wherein determining the value of the integral comprises accumulating, with the processor, a product of time and a difference between the physiological signal and a threshold value.

12. The method of claim 10, comprising determining, with the processor, a presence of a cluster in the one or more oxygen desaturation patterns.

13. The method of claim 10, wherein the one or more oxygen desaturation patterns each comprise a desaturation rate and a resaturation rate, and wherein the desaturation rate is slower than the resaturation rate.

14. The method of claim 10, wherein providing the indication of sleep apnea comprises providing the indication of sleep apnea as a visual display on a display of the patient monitor.

15. The method of claim 10, wherein providing the indication of another type of desaturation event comprises providing, with the processor, an audible alarm signal.

16. A method of evaluating a condition of a patient based on blood oxygen saturation data, the method comprising:
    driving, with a processor of a patient monitor, an emitter of a sensor to generate a physiological signal of a patient;
    receiving, with the processor, the physiological signal from the sensor;
    analyzing, with the processor, a physiological signal to determine a presence of one or more oxygen desaturation patterns;
    determining, with the processor, a value for an integral if the physiological signal is outside of a range or threshold;
    providing, with the processor, an indication of sleep apnea based at least in part upon both the presence of the one or more oxygen desaturation patterns and a determination that the value of the integral is greater than a first integral threshold; and providing, with the processor, an indication of another type of desaturation event based at least in part upon both an absence of the one or more oxygen desaturation patterns and a determination that the value of the integral is greater than a second integral threshold.

17. The method of claim 16, comprising displaying, with the processor, the indication of sleep apnea and the indication of another type of desaturation event on a display.

18. The method of claim 16, comprising providing, with the processor, an audible alarm to provide the indication of another type of desaturation event.

19. The method of claim 16, wherein determining the value of the integral comprises accumulating, with the processor, a product of time and a difference between the physiological signal and a threshold.

20. The method of claim 16, comprising determining, with the processor, a presence of a cluster in the one or more oxygen desaturation patterns.

* * * * *